United States Patent [19]

Gibbs et al.

[11] Patent Number: 5,470,832
[45] Date of Patent: Nov. 28, 1995

[54] INHIBITORS OF GERANYLGERANYL-PROTEIN TRANSFERASE

[75] Inventors: Jackson B. Gibbs, Chalfont; Samuel L. Graham, Schwenksville, both of Pa.

[73] Assignee: Merck & Co., Inc., Rahway, N.J.

[21] Appl. No.: 189,772

[22] Filed: Jan. 31, 1994

[51] Int. Cl.$^6$ .......................... A61K 38/00; C07K 5/00; C07K 7/00; C07K 17/00
[52] U.S. Cl. .......................... 514/18; 514/19; 530/331; 562/428; 562/556; 560/9; 560/16; 560/147
[58] Field of Search .................. 514/18–19; 530/331; 562/428, 556; 560/9, 16, 147

[56] References Cited

U.S. PATENT DOCUMENTS 5,238,922  8/1993  Graham et al. .................... 514/18

FOREIGN PATENT DOCUMENTS 535731  4/1993  European Pat. Off. .

OTHER PUBLICATIONS

Kohl et al. Science vol. 260 p. 1834 (1993).
Brown, M. S. and Goldstein, J. L., Mad Bet for Rab, (1993), Nature, 366, pp. 14–15.
Casey, P. J., Biochemistry of protein prenylation (1992), Journal of Lipid Research, 33, pp. 1731–1740.
Casey, P. J., et al., Enzymatic modification of proteins with a geranylgeranyl isoprenoid, (1991), Proc. Natl. Acad. Sci., USA, Biochemistry, 88, pp. 8631–8635.
Clarke, S., Protein Isoprenylation and Methylation At Carboxyl–Terminal Cysteine Residues, (1992), Annu. Rev. Biochem., 61, pp. 355–386.
Cox, A. D. and Der, CD. J., The Ras/Cholesterol Connection: Implications for Ras Oneogenicity, (1992), Critical Reviews in Oncogenesis, 3(4), pp. 365–400.
Gibbs, J. B., Ras C–Terminal Processing Enzymes—New Drug Targets?, (1991), Cell, 65, pp. 1–4.
Menard, L., et al., Rac1, a low–molecular–mass GTP–binding–protein with high intrinsic GTPase activity and distinct biochemical properties, (1992), Eur. J. Biochem., 206, pp. 537–546.
Moomaw, J. F. and Casey, P. J., Mammalian Protein Geranylgeranyltransferase, (1992), The Journal of Biological Chemistry, 267, No. 24, (Issue of Aug. 25), pp. 17438–17443.
Moores, S. L., et al., Sequence Dependence of Protein Isoprenylation, (1991), The Journal of Biological Chemistry, 266, No. 22, (Issue of Aug. 5), pp. 14603–14610.
Newmann, C. M. H. and Magee, A. I., Posttranslational processing of the ras superfamily of small GTP–binding proteins, (1993), Biochimica et Biophysica Acta. 1155, pp. 79–96.
Ridley, A. J. and Hall, A., The Small GTP–Binding Protein rho Regulates the Assembly of Focal Adhesions and Actin Stress Fibers in Response to Growth Factors, (1992), Cell, 70, pp. 389–399.
Ridley, A. J., et al., The Small GTP–Binding Protein rac Regulates Growth Factor–Induced Membrane Ruffling, (1992), Cell, 70, pp. 401–410.
Sato, Y., et al., High–performance size–exclusion chromatography and molar mass measurement by low–angle laser light scattering of recombinant yeast–derived human hepatitis B virus surface antigen vaccine particles, (1990), Journal of chromatography, 507, pp. 25–31.
Seabra, M. C., et al., Rab Geranylgeranyl Transferase, (1992) The Journal of Biological Chemistry, 267, No. 20 (Issue of Jul. 15), pp. 14497–14503.
Schulman, C. A., et al., Production of hepatitis B surface antigen (PreS2+S) by high–cell density cultivations of a recombinant yeast, (1991), Journal of Biotechnology 21, pp. 109–126.
Yokoyama, K., et al., A protein geranylgeranyltransferase from bovine brain: Implications for protein prenylation specificity, (1991), Proc. Natl. Acad. Sci., USA, 88, Biochemistry, pp. 5302–5306.
Reiss, Y., et al., Sequence requirement for peptide recognition by rat brain p21ras protein farnesyltransferase, (1991), Proc. Natl. Acad. Sci. USA, Biochemistry, 88, pp. 732–736.

Primary Examiner—Jill Warden
Assistant Examiner—Sheela J. Huff
Attorney, Agent, or Firm—David A. Muthard; Mark R. Daniel

[57] ABSTRACT

The compounds disclosed am analogs of the CAAX motif of proteins that can be modified by geranylgeranylation in vivo that selectively inhibit the geranylgeranylation of several proteins. The relatively poor activity of the compounds against the farnesyl protein transferase, which modifies several proteins important in cellular replication, allows the use of the compounds of the instant invention to treat diseases which which am regulated by the function of a geranylgeranylated protein, such as certain cancers and inflammatory diseases. Further contained in this invention are chemotherapeutic compositions containing these geranylgeranyl protein transfcrase type I inhibitors and methods for their production.

10 Claims, 2 Drawing Sheets

```
ACGATAGCGT TTTTTGCACT CTCCGGGCTG GATATGTTGG ATTCCTTAGA
TGTGGTGAAC AAAGATGATA TAATAGAGTG GATTTATTGG GTGCAGGTCC
TTCCCACAGA AGACAGATCA AATCTAAATC GCTGTGGTTT CCGAGGCTCT
TCATACCTGG GTATTCCGTT CAATCCATCA AAGGCTCCTG GAACAGCTCA
TCCTTATGAT AGTGGCCACA TTGCAATGAC CTACACTGGC CTCTCATGCT
TAGTTATTCT TGGAGACGAC TTAAGCCGAG TAAATAAAGA AGCTTGCTTA
GCGGGCTTGA GAGCCCTTCA GCTGGAAGAT GGAGTTTTT GTGCAGTACC
TGAAGGCAGT GAAAATGACA TCCGATTTGT GTACTGTGCT TCCTGTATTT
GCTATATGCT CAACAACTGG TCAGGCATGG ATATGAAAAA GCCATCACCT
ATATTAGAAG GAGTATGTCC TATGACAATG GACTGGCACA GGAGCTGGA
CTTGAATCTC ATGGAGGATC AACTTTTTGT GGCATTGCCT CACTATGTCT
GATGGGTAAA CTAGAAGAAG TTTTTTCAGA AAAAGAATTG AACAGGATAA
AGAGGTGGTG TATAATGAGG CAACAAAATG GTTATCATGG AAGACCTAAT
AAGCCTGTAG ACACCTGTTA TTCTTTTTGG GTGGGAGCAA CTCTGAAGCT
TCTAAAAATT TTCCAATACA CCAACTTCG
```

FIG. 1

```
GGATCCAGTA CTTATGGTAG CCACTGAGGA TGAGAGGCTA GCAGGGAGCGG
TGAGGGAGAG CGGCTGGATT TCTTACGGGA TCGGCACGTG CGATTTTTCC
AGCGCTGCCT CCAGGTTTTG CCGGAGCGCT ATTCTTCACT CGAGACAAGC
AGGTTGACAA TTGCATTTTT TGCACTCTCC GGGCTGGATA TGTTGGATTC
CTTAGATGTG GTGAACAAAG ATGATATAAT AGAGTGGATT TATTCCCTGC
AGGTCCTTCC CACAGAAGAC AGATCAAATC TAAATCGCTG TGGTTTCCGA
GGCTCTTCAT ACCTGGGTAT TCCGTTCAAT CCATCAAAGG CTCCTGGAAC
AGCTCATCCT TATGATAGTG GCCACATTGC AATGACCTAC ACTGGCCTCT
CATGCTTAGT TATTCTTGGA GACGACTTAA GCCGAGTAAA TAAAGAAGCT
TGCTTAGCGG GCTTGAGAGC CCTTCAGCTG GAAGATGGGA GTTTTTGTGC
AGTACCTGAA GGCAGTGAAA ATGACATGCG ATTTGTGTAC TGTGCTTCCT
GTATTTGCTA TATGCTCAAC AACTGGTCAG GCATGGATAT GAAAAAAGCC
ATCACCTATA TTAGAAGGAG TATGTCCTAT GACAATGGAC TGGCACAGGG
AGCTGGACTT GAATCTCATG GAGGATCAAC TTTTTGTGGC ATTGCCTCAC
TATGTCTGAT GGGTAAACTA GAAGAAGTTT TTTCAGAAAA AGAATTGAAC
AGGATAAAGA GGTGGTGTAT AATGAGGCAA CAAAATGGTT ATCATGGAAG
ACCTAATAAG CCTGTAGACA CCTGTTATTC TTTTTGGGTG GGAGCAACTC
TGAAGCTTCT AAAAATTTTC CAATACACTA ACTTTGAGAA AAATAGAAAT
TACATCTTAT CAACTCAAGA TCGCCTTGTA GGGGGATTTG CCAAGTGGCC
AGACAGTCAT CCAGATGCTT TGCATGCATA CTTTGGGATC TGTGGCCTGT
CACTAATGGA GGAAAGTGGA ATTTGTAAAG TTCATCCTGC TCTGAATGTA
AGCACACGGA CTTCTGAACG CCTTCTAGAT CTCCATCAAA GCTGGAAAAC
CAAGGACTCT AAACAATGCT CAGAGAATGT ACATATCTCC ACATGACTGA
TTTTAGATTG GGAGGGTGGG GGGGATTTGT AGCATAACTG TAGCTCAAGT
TTAAAAGCCA TGTATAACCA AGTGTGCTCT TTTTTTAAAA GGTAGAGTCT
TACAATCAAA TCTCCTGCTG ATTTCACTTT GGGATATGGT CTTGAGCCAG
TAATCTTTAT ACTGGGTTTC AAGAAAATCT TTGTTGAAGT TTGAACCACA
ACTTTGTCGT GGTTCTTAAA TGTTTATACT GTATTTCTAA GAAGTTGTTT
GAGGCAAATT AACTGTATGT GTGTAGGTTA TCTTTTTAAA AACTCTTCAG
TGCAAATTGT ATCTTATTAT AAAATGGACA CAAATTTTCA AGTTTACACT
TCATATAGCA TTGATAATCT TCAGGTGAAC ACTTAGTGAT CATTTAAAAA
GCTCACTGCT GATCGTAGAA AATTTGCTTT AATTAATTAA GTATCTGGGA
TTATTCTTTG AAAACAGATG ACCATAATTT TTTTTAAAGA AGAGTGACTT
ATTTTGTCTT ATTCTTAAG
```

FIG. 2

INHIBITORS OF GERANYLGERANYL-PROTEIN TRANSFERASE

BACKGROUND OF THE INVENTION

Prenylation of proteins by intermediates of the isoprenoid biosynthetic pathway represents a new class of post-translational modification (Glomset, J. A., Gelb, M. H., and Farnsworth, C. C. (1990). Trends Biochem. Sci. 15, 139–142; Maltese, W. A. (1990). FASEB J. 4, 3319–3328). This modification typically is required for the membrane localization and function of these proteins. Prenylated proteins share characteristic C-terminal sequences including CaaX (C, Cys; a, usually aliphatic amino acid; X, another amino acid), XXCC, or XCXC. Three post-translational processing steps have been described for proteins having a C-terminal CaaX sequence: addition of either a 15 carbon (farnesyl) or 20 carbon (geranylgeranyl) isoprenoid to the Cys residue, proteolytic cleavage of the last 3 amino acids, and methylation of the new C-terminal carboxylate (Cox, A. D. and Der, C. J. (1992a). Critical Rev. Oncogenesis 3:365–400; Newman, C. M. H. and Magee, A. I. (1993). Biochim. Biophys. Acta 1155:79–96). Some proteins may also have a fourth modification: palmitoylation of one or two Cys residues N-terminal to the farnesylated Cys. Proteins terminating with a XXCC or XCXC motif are modified by geranylgeranylation on the Cys residues and do not require an endoproteolytic processing step. While some mammalian cell proteins terminating in XCXC are carboxymethylated, it is not clear whether carboxymethylation follows prenylation of proteins terminating with a XXCC motif (Clarke, S. (1992). Annu. Rev. Biochem. 61,355–386). For all of the prenylated proteins, addition of the isoprenoid is the first step and is required for the subsequent steps (Cox, A. D. and Der, C. J. (1992a). Critical Rev. Oncogenesis 3:365–400; Cox, A.D. and Der, C. J. (1992b) Current Opinion Cell Biol. 4:1008–1016).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Clarke, 1992; Schafer, W. R. and Rine, J. (1992) Annu. Rev. Genet. 30:209–237). FPTase and GGPTase-I are α/β heterodimeric enzymes that share a common α subunit; the β subunits are distinct but share approximately 30% amino acid similarity (Brown, M. S. and Goldstein, J. L. (1993). Nature 366, 14–15; Zhang, F. L., Diehl, R. E., Kohl, N. E., Gibbs, J. B., Giros, B., Casey, P. J., and Omer, C. A. (1994). J. Biol. Chem. 269, 3175–3180). GGPTase. II has different α and β subunits and complexes with a third component (REP, Rab Escort Protein) that presents the protein substrate to the α/β catalytic subunits. Each of these enzymes selectively uses farnesyl diphosphate or geranylgeranyl diphosphate as the isoprenoid donor and selectively recognizes the protein substrate. FPTase farnesylates CaaX-containing proteins that end with Ser, Met, Cys, Gln or Ala. GGPTase-I geranylgeranylates CaaX-containing proteins that end with Leu or Phe. For FPTase and GGPTase-I, CaaX tetrapeptides comprise the minimum region required for interaction of the protein substrate with the enzyme. GGPTase-II modifies XXCC and XCXC proteins; the interaction between GGPTase-II and its protein substrates is more complex, requiting protein sequences in addition to the C-terminal amino acids for recognition. The enzymological characterization of these three enzymes has demonstrated that it is possible to selectively inhibit one with little inhibitory effect on the others (Moores, S. L., Schaber, M. D., Mosser, S. D., Rands, E., O'Hara, M. B., Garsky, V. M., Marshall, M. S., Pompliano, D. L., and Gibbs, J. B., J. Biol. Chem., 266:17438 (1991)).

The characterization of protein prenylation biology and enzymology has opened new areas for the development of inhibitors which can modify physiological processes. The prenylation reactions have been shown genetically to be essential for the function of a variety of proteins (Clarke, 1992; Cox and Der, 1992a; Gibbs, J. B. (1991). Cell 65: 1–4; Newman and Magee, 1993; Schafer and Rine, 1992). This requirement often is demonstrated by mutating the CaaX Cys acceptors so that the proteins can no longer be prenylated. The resulting proteins are devoid of their central biological activity. These studies provide a genetic "proof of principle" indicating that inhibitors of prenylation can alter the physiological responses regulated by prenylated proteins.

Protein geranylgeranyltransferase type-I (GGTase-I) transfers a geranylgeranyl group from the prenyl donor geranylgeranyl diphosphate to the cysteine residue of substrate proteins containing a C-terminal CAAX-motif in which the "X" residue is leucine or phenylalanine (Clark, 1992; Newman and Magee, 1993). Known targets of GGTase-I include the gamma subunits of brain heterotrimeric G proteins and Ras-related small GTP-binding proteins such as RhoA, RhoB, RhoC, CDC42Hs, Racl, Rac2, RaplA and RaplB (Newman and Magee, 1993; Cox and Der, 1992a). The proteins RhoA, RhoB, RhoC, Rac1, Rac2 and CDC42Hs have roles in the regulation of cell shape (Ridley, A. J. and Hall, A. (1992). Cell 70:389–399; Ridley, A. J., Paterson, H. F., Johnston, C. L., Keikmann, D., and Hall, A. (1992). Cell 70:401–410; Bokoch, G. M. and Der, C. J. (1993). FASEB J. 7:750–759). Rac and Rap proteins have roles in neutrophil activation (Bokoch and Der, 1993 ).

Activation of growth factor function and Ras function can cause tumor formation. Recently, it was demonstrated that the Rho and Rac proteins transmit intracellular signals initiated by growth factors and by Ras protein (Prendergast, G. C. and Gibbs, J. B. (1993). Adv. Cancer Res. 62, 19–64; Ridley and Hall, 1992; Ridley et al., 1992). Specifically, experiments demonstrated that the function of Rho and Rac proteins was required by Ras and growth factors to change cell shape, a biological parameter indicative of cellular transformation and cancer. Since Rho and Rac proteins require geranylgeranylation for function, an inhibitor of GGPTase-I would block the functions of these proteins and be useful as an anticancer agent.

Neutrophil activation is part of the body's inflammatory response. (Haslett, C. et al. Cur. Opinion Immunology, 2:10–18 (1989) Geranylgeranylated Rac and Rap proteins are required for this effect (Bokoch and Der (1993); Abo, A. et al., Nature, 353:668–670 (1991); Knaus, U.G. et al. Science, 254:1512–1515 (1991); Eklund, E. A. et al. J. Biol. Chem. 266:13964–13970 (I991); Quinn, M.T. et al. Nature, 342:198–200 (1989)), so an inhibitor of GGPTase-I will have antiinflammatory activity.

SUMMARY OF THE INVENTION

The present invention comprises analogs of the CAAX motif of proteins that can be modified by geranylgeranylation in vivo. These CAAX analogs inhibit the geranylgeranylation of several proteins. Furthermore, these CAAX analogues differ from previously described CAAX analogues (EP Pat. Publication 0 535 731 A2) in that they are more potent as inhibitors of geranylgeranyl protein transferase type I than the related enzyme Ras farnesyl protein transferase. The relatively poor activity against the farnesyl protein transferase, which modifies several proteins important in cellular replication, allows the use of the compounds of the instant invention to treat diseases which are regulated by the function of a geranylgeranylated protein. Further contained in this invention are chemotherapeutic compositions containing these geranylgeranyl transferase type I inhibitors and methods for their production.

The compounds of this invention are illustrated by the formulae:

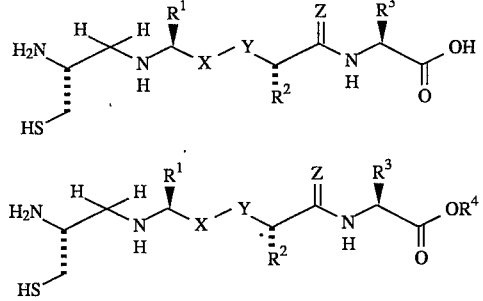

BRIEF DESCRIPTION OF THE DRAWINGS

FIG. 1. Nucleotide sequence of the 730 bp PCR product used in the cloning of the human GGPTase-I βGGI subunit. The human GGPTase-I βGGI subunit is employed to prepare recombinant human GGPTase-I which is employed in the in vitro evaluation of the instant compounds.

FIG. 2. Nucleotide, sequence of intermediate pRD566, which contains the complete coding sequence for human GGPTase-I βGGI and which is eventually translationally coupled to the coding sequence for human FPTase-α subunit to allow expression of human GGPTase-I.

DETAILED DESCRIPTION OF THE INVENTION

The compounds of this invention inhibit the geranylgeranylation of proteins by the enzyme geranylgeranyl protein transferase type I. In a first embodiment of this invention, the geranylgeranyl-protein transferase type I inhibitors are illustrated by the formula I:

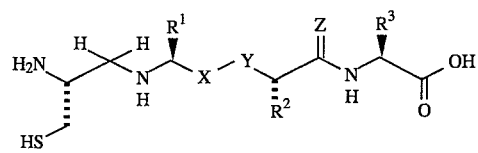

wherein:
R$^1$ and R$^2$ are independently selected from:
a) C$_2$–C$_8$ alkyl;
b) C$_2$–C$_8$ alkenyl;
c) C$_2$–C$_8$ alkynyl;
d) substituted C$_1$–C$_8$ alkyl;
e) aryl;
f) substituted aryl;
g) heteroaryl;
h) substituted heteroaryl; and
i) the side chain of a naturally occurring amino acid;

R$^3$ is selected from alkyl, alkenyl and alkynyl of 1 to 6 carbon atoms, either branched or straight chain, which is unsubstituted or substituted with a phenyl group;

X—Y is

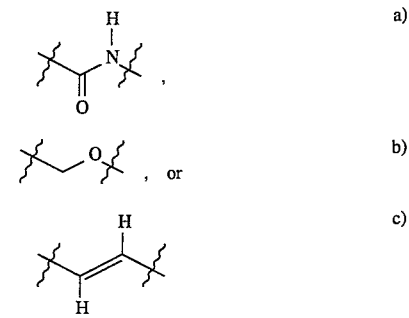

and Z is H$_2$ or O;
or the pharmaceutically acceptable salts thereof.

In a second embodiment of this invention are the prodrugs of compounds of formula I as illustrated by the formula II:

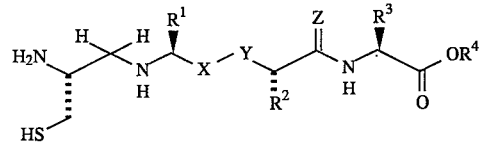

wherein:
R$^1$ and R$^2$ are independently selected from:
a) C$_2$–C$_8$ alkyl;
b) C$_2$–C$_8$ alkenyl;
c) C$_2$–C$_8$ alkynyl;
d) substituted C$_1$–C$_8$ alkyl;
e) aryl;
f) substituted aryl;
g) heteroaryl;
h) substituted heteroaryl; and
i) the side chain of a naturally occurring amino acid;

R$^3$ is selected from alkyl, alkenyl and alkynyl of 1 to 6 atoms either branched or straight chain which is unsubstituted or substituted with a phenyl group;

X—Y is

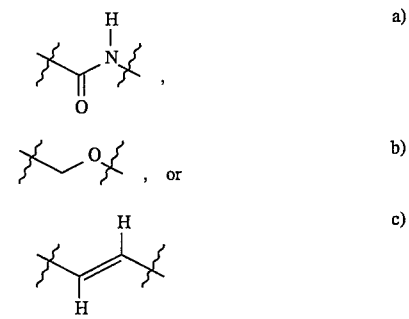

R$^4$ is selected from:
a) C$_1$–C$_8$ alkyl;
b) C$_3$–C$_8$ alkenyl;
c) C$_3$–C$_8$ alkynyl;
d) substituted C$_1$–C$_8$ alkyl;
e) aryl;
f) substituted aryl;
g) heteroaryl; and h) substituted heteroaryl;

and Z is $H_2$ or O;

or the pharmaceutically acceptable salts.

The preferred compounds of this invention are as follows:

N-(2(R)-amino-3-mercaptopropyl)-valyl-isoleucyl-leucine;

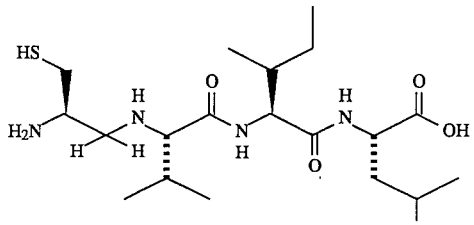

N-(2(R)-amino-3-mercaptopropyl)-valyl-isoleucyl-leucine methyl ester;

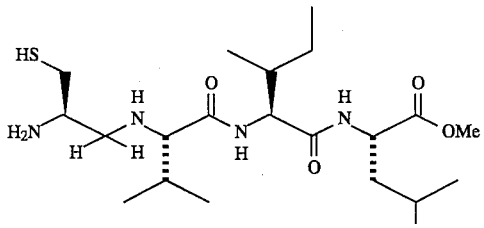

N-[5(S)-(2(R)-amino-3-mercaptopropylamino)-6(S)-methyl-2(R)-isopropyl-3,4(E)-heptenoyl]-leucine;

N-[5(S)-(2(R)-amino-3-mercaptopropylamino)-6(S)-methyl-2(R)-isopropyl-3,4(E)-heptenoyl]-leucine methyl ester;

N-[2(S)-(2(S)-(2(R)-amino-3-mercaptopropylamino)-3(S)-methylpentyloxy)-3-methylbutanoyl]-leucine;

N-[2(S)-(2(S)-(2(R)-amino-3-mercaptopropylamino)-3(S)-methylpentyloxy)-3methylbutanoyl]-leucine methyl ester;

or the pharmaceutically acceptable salts thereof.

In the present invention, the amino acids which are disclosed are identified both by conventional 3 letter and single letter abbreviations as indicated below:

| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention. The present invention further includes all disulfides of the claimed compounds, derived from two of the same compounds.

When any variable (e.g. aryl, heterocycle, $R^1$, $R^2$ etc.) occurs more than one time in any constituent, its definition on each occurence is independent at every other occurrence. Also, combinations of substituents/or variables are permissible only if such combinations result in stable compounds.

As used herein, the term "alkyl" includes cyclic, branched and straight-chain saturated aliphatic hydrocarbon groups having the specified number of carbon atoms up to 20 carbon atoms. Examples of alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like.

The term "cycloalkyl" refers to a hydrocarbon ring having from 3 to 7 carbon atoms. Examples of cycloalkyl groups are cyclopropyl, cyclopentyl, cycloheptyl and the like.

As used herein, the term "alkenyl" includes both branched and straight-chain aliphatic hydrocarbon groups containing one or two double bonds and having the specified number of carbon atoms up to 20 carbon atoms. Examples of alkenyl groups include vinyl, allyl, 3-butenyl, 2-pentenyl, 3-pentenyl, and the like.

As used herein, the term "alkynyl" includes both branched and straight-chain aliphatic hydrocarbon groups containing one triple bond and having the specified number of carbon atoms up to 20 carbon atoms. Examples of alkynyl groups include 2-pentynyl, hexynyl and the like.

The term "alkoxy" as used herein represents an alkyl group of indicated number of carbon atoms attached through an oxygen bridge. The terms "halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term "heteroaryl", as used herein, represents a stable 5- to 7-membered monocyclic or stable 8- to 11-membered bicyclic ring which is unsaturated, and which consists of carbon atoms and from one to four heteroatoms selected from the group consisting of N, O, and S. The heterocyclic ring may be attached at any heteroatom or carbon atom which results in the creation of a stable structure. Examples of such heterocyclic elements include, but are not limited to, benzimidazolyl, benzothienyl, furyl, imidazolyl, indolyl, isoquinolinyl, pyridyl, quinolinyl, thienyl and the like.

The term "substituted" as applied to alkyl, alkenyl, alkynyl, aryl or heteroaryl means that moiety has 1 or 2 substituents selected from $C_1$–$C_6$ alkyl, hydroxy, alkoxy, substituted or unsubstituted aryl, substituted or unsubstituted heteroaryl, —$NO_2$, —$SCF_3$, halogen, —$CO_2H$, —$CO_2$-alkyl, —CN or —$CF_3$. It is understood that the term "substituted alkyl" does not include the side chain of a naturally occuring amino acid.

The term "a side chain of a naturally occurring amino acid" includes those substituents attached to the α-carbon of naturally occuring amino acids and includes methyl, —$CH_2CONH_2$, —$CH_2CO_2H$, —$CH_2SH$, —$CH_2CH_2CO_2H$, 4-imidazolylmethyl, isopropyl, —$CH_2CH_2SCH_3$, benzyl, hydroxymethyl and the like. The term also includes oxidized forms of such sidechains such as the side chain of methionine sulfoxide or methionine sulfone The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, steafic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifiuoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et at., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference. Abbreviations used in the description of the chemistry and in the Examples that follow are:

| | |
|---|---|
| $Ac_2O$ | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide hydrochloride; |
| HOBT | 1-Hydroxybenzotriazole hydrate; |
| $Et_3N$ | Triethylamine; |
| EtOAc | Ethyl acetate. |
| FAB | Fast atom bombardment; |
| HOOBT | 3-Hydroxy-1,2,3-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide |
| Py | Pyridine; |
| TFA | Trifluoroacetic acid; |
| THF | Tetrahydrofuran; |

Compounds of this invention are prepared by employing the reactions shown in the following Reaction Schemes A–D, in addition to other standard manipulations such as ester hydrolysis, cleavage of protecting groups, etc., as may be known in the literature or exemplified in the experimental procedures. Some key bond-forming and peptide modifying reactions are:

Reaction A

Amide bond formation and protecting group cleavage using standard solution or solid phase methodologies.

Reaction B

Preparation of a reduced peptide subunit by reductive alkylation of an amine by an aldehyde using sodium cyanoborohydride or other reducLng agents.

These reactions may be employed in a linear sequence to provide the compounds of the invention or they may be used to synthesize fragments which are subsequently joined by the alkylation reactions described in the Reaction Schemes.

REACTION SCHEME A
Reaction A. Coupling of residues to form an amide bond

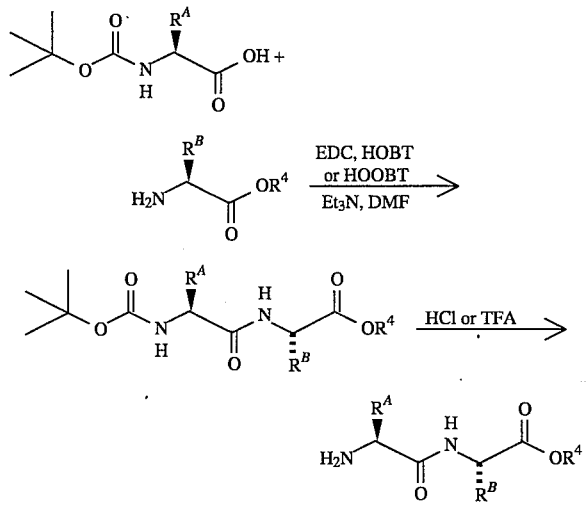

REACTION SCHEME B
Reaction B. Preparation of reduced peptide subunits by reductive alkylation

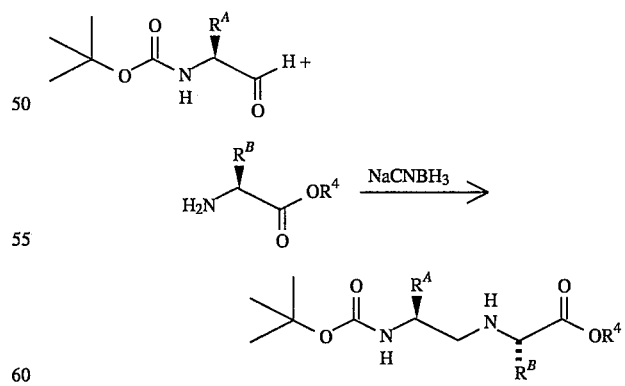

where $R^A$ and $R^B$ are $R^1$, $R^2$ or $R^3$ as previously defined, including their protected fonns compatible with the reaction conditions shown, for example, the triphenylmethyl (trityl) protected side chain of cysteine.

Certain compounds of this invention wherein X—Y is an ethenylene unit are prepared by employing the reaction sequences shown in Reaction Scheme C. Reaction Scheme C outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. The key reactions are: stereoselective reduction of the Boc-amino-enone to the corresponding syn amino-alcohol (Scheme C, Step B, Part 1 ), and stereospecific boron trifluoride or zinc chloride activated organo-magnesio, organo-lithio, or organo-zinc copper(l) cyanide $S_N2'$ displacement reaction (Scheme C, Step G). Through the use of optically pure N-Boc amino acids as starting material and these two key reactions, the stereochemistry of the final products is well defined. In Step H of Scheme C, the cysteine-derived fragment is added using a protected cysteinal and a reducing agent. Finally, the methyl ester is saponified and the protecting groups are cleaved. The order of these final steps is not critical, recognizing only that when base hydrolysis is performed last, the compound substantially forms the symmetrical disulfide.

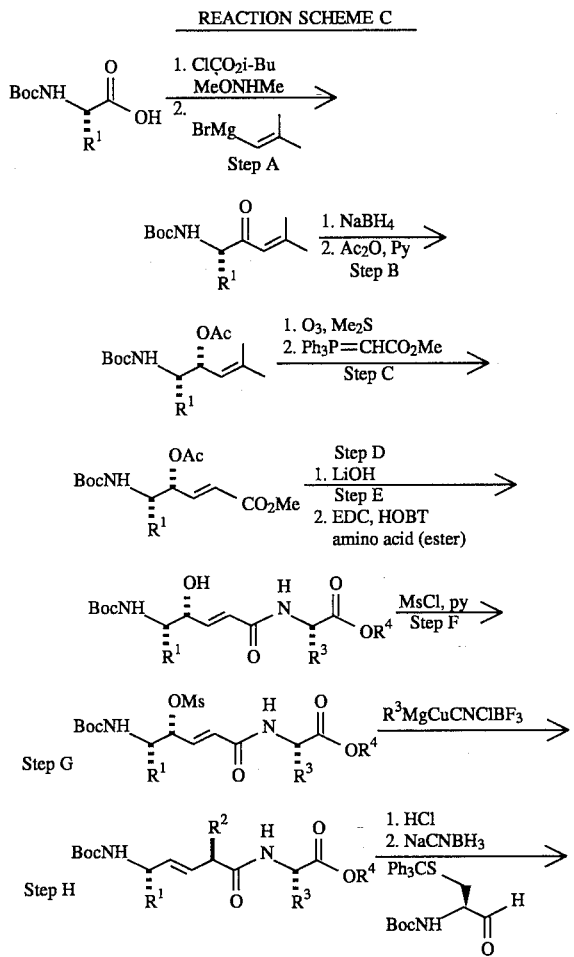

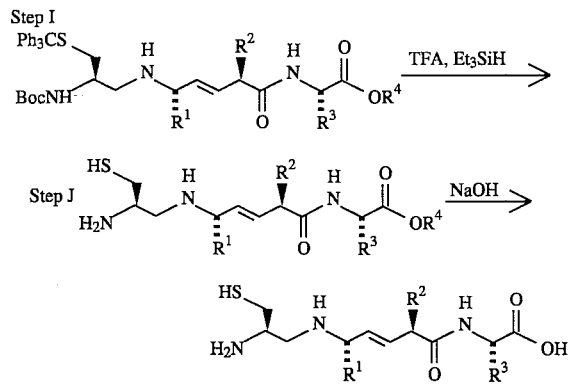

The oxa isostere compounds of this invention are prepared according to the route outlined in Scheme D. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. The N-Boc derivative 4 is then obtained by the treatment of 3 with BOC anhydride and DMAP (4-dimethylaminopyridine) in methylene chloride. Alkylation of 4 with $R^2X^L$, where $X^L$ is a leaving group such as Br—, I—or Cl—, in THF/DME (1,2-dimethoxyethane) in the presence of a suitable base, preferably NaHMDS [sodiron bis(trimethylsilyl)amide], affords 5, which is retreated with NaHMDS followed by protonation to give 6. Alternatively, 6a can be prepared from 4 via an aldol condensation approach. Namely, deprotonation of 4 with NaHMDS followed by the addition of a carbonyl compound $R^5R^6CO$ gives the adduct 7. Dehydration of 7 can be effected by mesylation and subsequent elimination catalyzed by DBU (1,8-diazabicyclo[5.4.0]undec-7-ene) or the direct treatment of 7 with phosphorus oxychloride in pyridine to give olefin 8. Then, catalytic hydrogenation of 8 yields 6a. Direct hydrolysis of 6 with lithium hydrogen peroxide in aqueous THF will produce acid 9b. Sometimes, it is more efficient to carry out this conversion via a 2-step sequence, namely, hydrolysis of 6 in hydrochloric acid to afford 9a, which is then derivatized with BOC-ON or BOC anhydride to give 9b. Amide bond formation between acid .9b and the ester of an amino acid is carried out under the conditions exemplified in the previously described references to yield derivative 10. Treatment of 10 with gaseous hydrogen chloride and reductive alkylation with the protected cysteine-derived aldehyde (11 ) and a reducing agent (e.g., sodium cyanoborohydride) gives 12. Cleavage of the protecting groups gives 13 and hydrolysis to the corresponding acid 14 is accomplished by standard methods such as treatment with NaOH in alcoholic or aqueous milieux followed by careful acidification with dilute HCl. It is also possible to saponify the ester prior to removal of the amino-terminal protecting groups.

SCHEME D
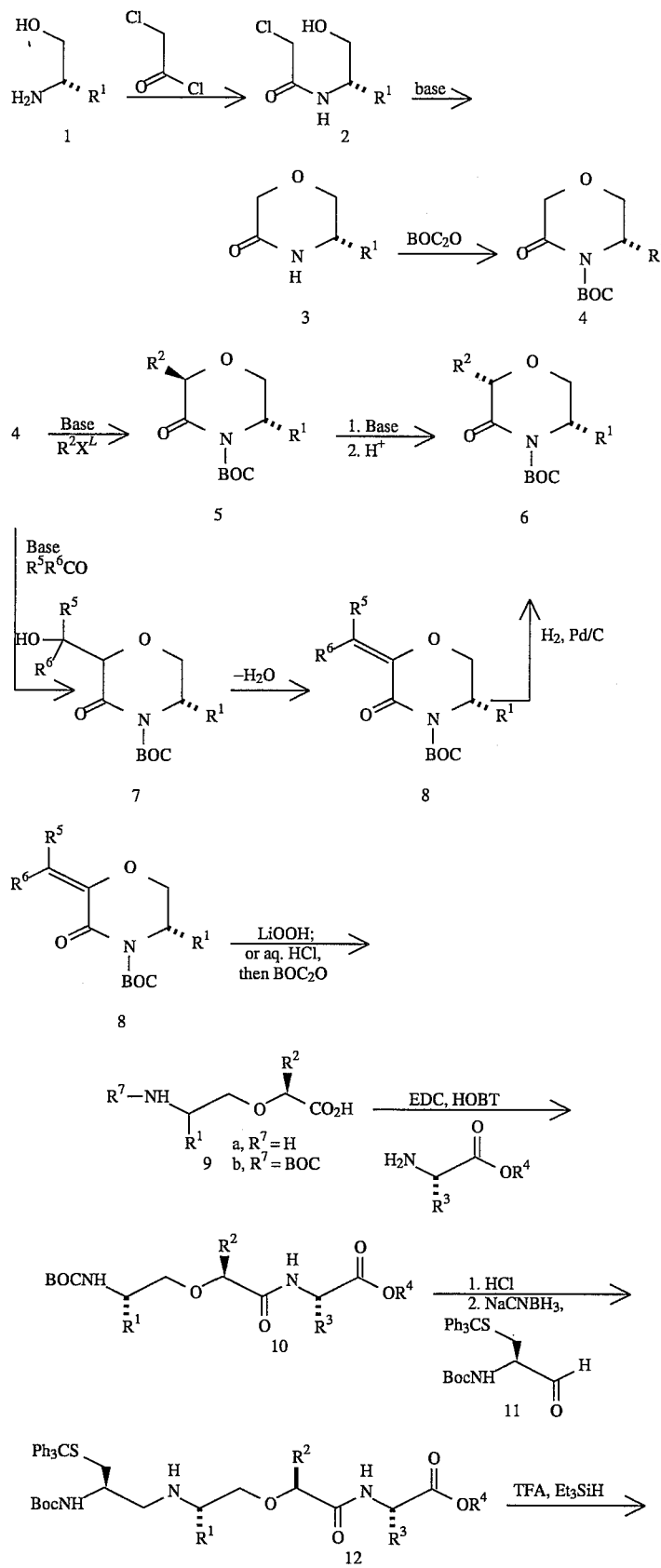

-continued
SCHEME D

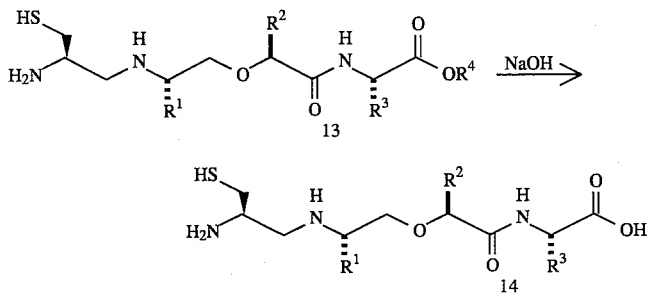

The compounds of this invention inhibit geranylgeranyl protein transferase, which catalyzes the first step in the post-translational processing of several proteins. These compounds are useful as pharmaceutical agents for mammals, especially for humans. These compounds may be administered to patients for use in the treatment of abnormal cellular proliferative diseases and cancer. Such cancers include but are not limited to growth factor stimulated cancers, such as breast carcinomas activated by erb B2, and the like, and Ras regulated cancers, such as colon cancer, pancreatic cancer and the like. The compounds of the instant invention may furthermore be administered to patients for use in the treatment of inflammatory diseases which are regulated by NAPDH oxidase, those diseases in which tissue damage is mediated by phagocytes (neutrophils, macrophages, eosinophils). Such inflammatory diseases include rheumatoid arthitis, inflammatory bowel disease, interstitial pulmonary edaema, myocardial infarction, cystic fibrosis and the like.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspe, nsions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions shotaid be suitably adjusted and buffered. For intravenous use, the total concentration of solutes should be controlled in order to render the preparation isotonic.

The present invention also encompasses a pharmaceutical composition useful in the treatment of certain cancers and inflammatory diseases comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

In another exemplary application, a suitable amount of compound is administered to a mammal undergoing treatment for an inflammatory disease. The magnitude of prophylactic or therapeutic dose of a compound of Formula I will, of course, vary with the nature of the severity of the condition to be treated and with the particular compound of Formula I and its route of administration. In general, for anti-inflammatory use, administration occurs in an amount between about 0.1 mg/kg of body weight to about 100 mg/kg of body weight per day, preferably of between 0.5 mg/kg of body weight to about 10 mg/kg of body weight per day. On the other hand, it may be necessary to use dosages outside these limits in some cases.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

Preparation of
N-(2(R)amino-3-mercaptopropyl)-valyl-isoleucyl-leucine methyl ester Step A. Preparation of N-(2(R)-t-butoxycarbonyl-amino-3-triphenyl-methylmercaptopropyl)-valyl-isoleucyl-leucine methyl ester.

The tripeptide ester valyl-isoleucyl-leucine methyl ester was synthesized using conventional solution phase peptide synthesis methods. The trifluoroacetate salt of this tripeptide (360 mg, 0.77 mmol) was dissolved in 5 mL of methanol with 147 mg (1.5 mmol) of potassium acetate and 670 mg( 1.5 mmol) of N-Boc-S-tritylcysteinal (prepared using the procedure of Goel, Krolls, Stier, and Kesten Org. Syn. 67:69–74 (1988) for the preparation of N-Boc-leucinal) was added. Sodium cyanoborohydride (47 mg, 0.75 mmol) was added and the mixture was stirred overnight. The mixture was diluted with ether and washed with water, 5% ammonium hydroxide and brine. The solution was dried (sodium sulfate) and evaporated to give a white foam which was purified by chromatography (1–15% acetone in methylene chloride). The title compound was obtained as an oily material.

Step B. Preparation of N-(2(R)-amino-3-mercaptopropyl)-valyl-isoleucyl-leucine methyl ester.

A sample of the protected pseudopeptide prepared as described in Step A (728 mg, 0.92 mmol) was dissolved in 100 mL of methylene chloride, 50 mL of TFA was added and the resulting yellow solution was treated immediately with 0.80 mL (5 mmol) of triethylsilane. After 45 min, the solvents were evaporated and the residue was partitioned between hexane and 0.1% aqueous TFA. The aqueous solution was lyophilized. This material was further purified by reverse phase HPLC (5–95% acetonitrile/0.1% TFA/ water) to afford the title compound.

$^1$H NMR (CD$_3$OD) δ8.65 (1H, d), 4.45 (1H, m), 4.3 (1H, d), 3.7 (3H, s), 3.4 (1H, m), 3.15 (1H, d), 2.75–2.95 (m), 0.8–1.05 (18 H, m). FAB mass spectrum, m/z=447 (M+1). Anal. Calcd for C$_{21}$H$_{42}$N$_4$O$_4$S . 1.8 TFA: C, 45.24; H, 6.75; N, 8.56. Found: C, 45.26; H, 6.77; N. 8.50.

Example 2

N-(2(R)-amino-3-mercaptgpropyl)-valyl-isoleucyl-leucine;

Step A. Preparation of N-(2(R)-t-butoxycarbonylamino-3-triphenylmethylmercaptopropyl)-valyl-isoleucyl-leucine The producl of Example 1, Step A (60 mg, 0.076 mmol) was dissolved in 1 mL of methanol and 150 μL of 1N NaOH was added. After stirring overnight, the solution was acidified with 150 μL of 10% citric acid and the product was extracted with ether. The ether solution was washed with water and brine and dried (sodium sulfate). Evaporation provided the title compound as a solid.

Step B. Preparation of N-(2(R)-amino-3-mercaptopropyl)-valyl-isoleucyl-leucine

Using the method of Example 1, Step B, the protecting groups were removed with TFA and triethylsilane to provide the title compound. FAB mass spectrum, m/z=433 (M+1). Anal. Calcd for C$_{20}$H$_{40}$N$_4$O$_4$S . 2 TFA: C, 43.63; H, 6.41; N, 8.48. Found: C, 43.26; H, 6.60; N. 8.49.

Example 3

Preparation of
N-[5(S)-(2(R)-amino-3-mercaptopropylamino)-6(S)-methyl-2(R)-isopropyl- 3,4(E)-heptenoyl]-leucine methyl ester;

Step A. Preparation of 3(S)-N-tert-(butyloxy)carbonylamino-2,6-dimethyl-5,6-hepten-4-one To a cold (0 ° C.) solution of N-t-(butoxy)carbonyl-L-valine (12 g, 55.2 mmol) in ethyl acetate (180 mL), N-methyl morpholine (6.1 mL, 55.2 mmol) and isobutyl chloroformate (7.16 mL, 55.2 mmol) were added successively. The resultant white suspension was stirred at 0 ° C. for 15 min, treated with N,O-dimethylhydroxylamine hydrochloride (5.39 g, 55.2 mmol) and N-methylmorpholine (6.1 mL, 55.2 mmol), and then stirred at room temp. overnight. The resultant mixture was washed successively with water, 10% aqueous citric acid, brine, and was dried over anhydrous magnesium sulfate, filtered and concentrated. The residual oil was chromatographed on silica gel eluting with 20% ethyl acetate in hexane. Collection and concentration of appropriate fractions provided 11.07 g (73%) of the corresponding amide.

A 1 liter three neck round bottom flask was charged with magnesium turnings (44 g, 1.8 mol) and timed dried under a steady stream of dry argon. The turnings were activated.up by stirring under an atmosphere of argon for an additional 3 to 4 hours at room temp. Tetrahydrofuran (450 mL), freshly distilled from sodium benzophenone ketyl, 2-methylpropenyl bromide (50 g, 0.37 mol), and a crystal of iodine were added. The mixture was warmed gently with a mantle until slight reflux occurred. Without removing the mantle, heating was discontinued and the mixture was stirred overnight under an atmosphere of argon.

The Grignard reagent was added to a cold (–50 ° C.) solution of N-tert-(butoxy)carbonylvaline N,O-dimethylhydroxylamide (11 g, 42 mmol) in tetrahydrofuran (300 mL) over a period of 20 min maintaining the temperature below –40 ° C. The mixture was allowed to warm slowly to room temp. The solution was diluted with diethyl ether, treated with 10% aqueous citric acid, washed with brine, dried over magnesium sulfate, filtered, and concentrated in vacuo. The residual oil was chromatographed on silica gel eluting with 15% ethyl acetate in hexane. Collection and concentration of appropriate fractions provided the title compound.

Step B. Preparation of 3(S)-N-tert-(butyloxy)carbonylamino-4(R)-acetoxy-2,7-dimethyl-5,6-heptene To a cold (0° C.) solution of 3(S)-N-tert-(butyloxy)carbonylamino- 2,6-dimethyl-5,6-hepten-4-one (7.9 g, 30.9 mmol) in methanol (150 mL), sodium borohydride was added portionwise until reaction was complete as monitored by tlc on silica gel eluting with 20% ethyl acetate in hexane. The resultant mixture was concentrated under vacuo. The residue was suspended in diethyl ether, washed successively with 1M aqueous hydrochloric acid and brine, dried over magnesium sulfate, filtered and concentrated in vacuo to provide the corresponding alcohol.

Without further purification, the crude alcohol, 4-N,N-dimethyl-aminopyridine (95 mg), and pyridine (15 mL) were dissolved in dichloromethane (40 mL), cooled to 0 ° C. and treated with acetic anhydride (15 mL). The resultant mixture was stirred at room temp for 2 h and concentrated under vacuo. The residual oil was chromatographed on silica gel eluting with 20% ethyl acetate in hexane. Collection and concentration of appropriate fractions provided the acetate as a white solid.

Step C. Preparation of methyl 5(S)-N-tert-(butyloxy)carbonylamino- 4(R)-acetoxy-6-methyl-2,3-E-heptenoate To a cold (–78 ° C.) solution of 3(S)-N-tert-(butyloxy)carbonylamino- 4(R)-acetoxy-2,7-dimethyl-5,6-heptene (9.47 g, 31.6 mmol) in dichloromethane (140 mL), a steady stream of ozone was bubbled through until a blue, color persisted. The mixture was stirred for an additional 5 min and purged with argon to remove excess ozone. Then dimethyl sulfide (23 mL) was added and the reaction mixture was allowed to warm to room temp. The resultant mixture was cooled back to −78 °C, and (carbomethoxymethylene)-triphenylphosphorane (23.3 g, 69.6 mmol) was added. The mixture was stirred at room temp overnight and concentrated onto silica gel (20 g). The resultant solid was loaded on a column of silica gel saturated with 20% ethyl acetate in hexane, and the column eluted with the same solvent mixture. Collection and concentration of appropriate fractions provided the heptenoate.

Step D. Preparation of 5(S)-N-tert-(butyloxy)carbonylamino-4(R)-hydroxy-6-methyl-2,3-E-heptenoic acid.

To a solution of methyl 5(S)-N-tert-(butyloxy)carbonylamino-4(R)-acetoxy- 6-methyl-2,3-E-heptenoate (9.62 g, 29.24 mmol) in tetrahydrofuran (20 mL), a saturated solution of lithium hydroxide (5 g) in methanol-water, 3:1 v/v, was added. The mixture was then made homogenous by addition of minimum amount of methanol-water (3:1 v/v. mixture) and stirred at room temp for 2 days. The resultant solution was acidified with aqueous hydrochloric acid to pH 5 and concentrated in vacuo. The residue was passed through a small plug of silica gel eluting with 20% methanol in chloroform. Collection and concentration of appropriate fractions provided the corresponding hydroxyacid.

Step E. Preparation of 5(S)-N-tert-(butyloxy)carbonylamino-4(R)-hydroxy-6-methyl-2,3-E-heptenoyl-leucine methyl ester To a solution of 5(S)-N-tert-(butyloxy)carbonylamino-4(R)-hydroxy-6(S)-methyl-2,3-E-heptenoic acid (0.40 g, 1.39 mmol) in dimethylformamide (6 mL), 1-(3-dimethylaminopropyl)-3-ethylcarbodiimide hydrochloride (0.40 g, 2.09 mmol), 1hydroxybenzotriazole hydrate (0.28 g, 2.09 mmol), L-leucine methyl ester hydrochloride (0.76, 4.18 mmol), and diisopropylethylamine (0.68 mL, 3.9 mmol) were added. The resultant mixture was stirred at room temperature overnight, and concentrated under vacuo. The residue was diluted with ethyl acetate, and the organic solution washed successively with water, 10% aqueous citric acid, brine, dried over magnesium sulfate, filtered and concentrated. The residue was then subjected to column chromatography on silica gel eluting with 5% methanol in chloroform. Collection and concentration of appropriate fractions provided the coupled product.

Step F. Preparation of 5(S)-N-tert-(butyloxy)carbonylamino-4(R)-(methylsulfonyl)oxy-6-methyl- 2,3-E-heptenoyl-leucine methyl ester.

To a cold (−20° C.) solution of 5(S)-N-tert-(butyloxy)carbonylamino- 4(R)-hydroxy-6-methyl-2,3-E-heptenoyl leucine methyl ester (0.39 g, 0.98 mmol) in a mixture of dichloromethane (2 mL) and pyridine (1 mL), methanesulfonyl chloride (0.5 mL) was added. The resultant mixture was kept at 0° C. ovenight, and concentrated under vacuo. The residue was diluted with dichloromethane, washed successively with sat. sodium bicarbonate, and brine. The organic phase was dried over magnesium sulfate, filtered and concentrated. The residue was subjected to column chromatography on silica gel eluting with a mixture of ethyl acetate and hexane, 8:2 v/v. Collection and concentration of appropriate fractions provided the mesylate, which is stable for storage at −10° C.

Step G. Preparation of 5(S)-N-tert-(butyloxy)carbonylamino-6-methyl-2-(R)-i-propyl- 3,4-E-heptenoyl-leucine methyl ester To a cold (−78° C.) suspension of copper(I) cyanide (0.17 g, 1.9 mmol) in tetrahydrofuran (20 mL, freshly distilled from sodium benzophenone ketyl), a solution of i-propyl-magnesium chloride (0.94 mL, 2.0M, 1.9 mmol) in tetrahydrofuran was added. The mixture was stirred at 0° C. until a homogeneous solution was formed. Once a solution was formed, it was cooled to −78° C., boron-trifluoride etherate (0.24 mL, 1.9 mmol) was added, and the resulting mixture was stirred at −78° C. for 7 min. A solution of 5(S)-N-tert-(butyloxy)carbonylamino- 4(R)-(methylsulfonyl)oxy-6-methyl-2,3-E-heptenoyl leucine methyl ester (0.15 g, 0.31 mmol) in tetrahydrofuran (15 mL) was added dropwise to the above mixture. The resultant solution was stirred at −78° C. for 3h, quenched with sat. aqueous ammonium chloride (pH 8) and diluted with diethyl ether. The organic solution was washed with brine, dried over magnesium sulfate, filtered, and concentrated. The residue was chromatographed on silica gel eluting with 60% ethyl acetate in hexane. Collection and concentration of appropriate fractions provided the 3,4-E-heptenoyl-leucine methyl ester.

Step H. 5(S)-[2(R)-N-tert-(butyloxy)carbonyl amino-3-S-triphenylmethylmercapto-propylamino]- 6-methyl-2(R)-i-propyl-3,4-E-heptenoyl-leucine methyl ester.

To a cold (0° C.) solution of 5(S)-N-tert-(butyloxy)-carbonylamino- 6-methyl-2(R )-i-propyl-3,4-E-heptenoyl-leucine methyl ester (82 mg, 0.19 mmol) in a mixture of ethyl acetate (10 mL) and dichloromethane (10 mL), a steady stream of anhydrous hydrogen chloride gas was bubbled through for a period of 10 min. The mixture was capped and stirred for an additional 40 min at 0° C. The resultant solution was than purged with a stream of argon and concentrated under vacuum to provide the corresponding hydrochloride salt.

The above amino-heptenoylamide HCl salt, N-tert-(butyloxy)carbonyl-S-triphenylmethyl-L-cysteine aidehyde (223 mg, 0.5 mmol) and molecular sieves (3A, powder) were combined in methanol (6 mL), The pH was adjusted to 5 by addition of acetic acid at room temp, sodium cyanoborohydride (19 mg, 0.3 mmol) was added and the mixture was stirred at room temp overnight. The resultant slurry was filtered and concentrated. The residue was diluted with ethyl acetate, washed with brine, dried over magnesium sulfate, filtered, and concentrated under vacuo. The residue was chromatographed on silica gel eluting with 10% ethyl acetate in hexane to afford the coupled product.

Step I. Preparation of 5(S)-[2(R)-amino-3-mercapto-propylamino]-6-methyl- 2(R)-i-propyl-3,4-E-heptenoyl-leucine methyl ester To a solution of 5(S)-[2(R)-N-tert-(butyloxy)carbonylamino- 3-S-triphenylmethylmercapto-propylamino]-6-methyl-2(R)-i-propyl- 3,4-E-heptenoyl-leucine methyl ester (40 mg, 54 µmol) in a mixture of dichloromethane (1.4 mL) and trifluoroacetic acid (0.7 mL) at room temp, triethylsilane (34 µL, 21 µmol) was added. The resultant solution was stirred at room temp. for 1 h, and concentrated under vacuo. The residue was dissolved in a mixture of 0.1% aqueous trifluoroacetic acid (5 mL) and hexane (2 mL). The aqueous layer was washed four more times with hexane, stirred under reduced pressure to remove residual hexane, and lyophilized overnight to provide the desired product as the trifluoroacetate salt. Anal. Calcd for $C_{20}H_{41}$ $O_3N_3S$ . 2.3 $CF_3COOH$: C, 45.36; H, 6.44; N, 6.20. Found: C, 45.22; H, 6.50; N, 6.49.

Example 4

Preparation of
5(S)-[2(R)-amino-3-mercaptopropylamino]-6-methyl
(R)-i-propyl- 3,4-E-heptenoyl-leucine To a solution of 5(S)-[2(R)-amino-3-mercaptopropylamino]-6-methyl-(R)-i-propyl- 3,4-E-heptenoyl-leucine methyl ester (the product of Example 3, 2.62 mg, 3.86 gmol) in methanol (50 μL), an aqueous solution of sodium hydroxide (15.5 μL, 1.00M) was added. After standing a room temp for 1 h, the solution was diluted with methanol to 10 mM. HPLC analysis confirmed complete conversion of the methyl ester to the corresponding acid.

Example 5

Preparation of
N-[2(S)-(2(S)-(2(R)-amino-3-mercaptopropylamino)-3(S)-methylpentyloxy)-3-methylbutanoyl]-leucine methyl ester;

Step A. Preparation of N-(alpha-chloroacetyl)-L-isoleucinol

To a stirred solution of L-isoleucinol (20 g, 0.17 mol) and triethylamine (28.56 ml, 0.204 mol) in $CH_2Cl_2$ (500 ml) at −78° C. was added chloroacetyl chloride (16.3 ml, 0.204 mol) over 5 minutes. The cooling bath was removed and the solution allowed to warm to −20° C. The mixture was diluted with EtOAc and washed sequentially with 1M HCl, and brine and dried ($Na_2SO_4$). Evaporation in vacuo afforded the amide title compound.

Rf=0.3 $CH_2Cl_2$: MeOH (95:5); $^1H$ NMR (CDCl3) δ6.80 (1H, brd, J=5 Hz), 4.10 (2H, s), 3.84 (1H, m), 3.79 (2H, m), 2.65 (1H, brs), 1.72 (1H, m), 1.55 (1H, m), 1.17 (1H, m), 0.96 (3H, d, J = 6Hz) 0.90 (3H,t, J=6 Hz).

Step B. Preparation of 5(S)-[ 1 (S)-methyl]propyl-2,3,5,6-tetrahydro-4H- 1,4-oxazin-3-one To a stirred solution of N-(alpha-chloroacetyl)-L-isoleucinol (7.4 g, 0.038 mol) in THF (125 ml) under argon at 0° C. was slowly added sodium hydride (2.2 g of a 60% dispersion in mineral oil, 0.055 mol) with concotnitant gas evolution. After completing the addition, the mixture was warmed to room temperature (R.T.) and stirred for 16 hr. Water (2.8 ml) was added and the solvents evaporated in vacuo. The residue was dissolved in $CHCl_3$ (70 ml) and washed with water and saturated NaCl solution. The organic layer was dried ($Na_2SO_4$) and evaporated in vacuo. The residue was chromatographed using silica gel eluting with $CH_2Cl_2$: MeOH (96:4) to afford the lactam title compound as a white solid.

Rf=0.35 $CH_2Cl_2$.MeOH (95:5); $^1H$ NMR δ(CDCl_3) 6.72 (1H, brs), 4.20 (1H, d, J= 14.5 Hz), 4.10 (1H, d, J=14.5 Hz), 3.88 (1H, dd, J = 9 and 3.5 Hz), 3.58 (1H, dd, J= 9 and 6.5 Hz), 3.45 (1H, brqt, J= 3.5 Hz), 1.70–1.45 (2H, m), 1.34–1.15 (1H, m), 0.96 (3H, t, J=: 6.5 Hz), 0.94 (3H, d, J= 6.5 Hz).

Step C. Preparation of N-(tert-butoxycarbonyl)-5(S)-[1(S)-methyl]-propy[-2,3,5,6-tetrahydro- 4H- 1,4-oxazin-3-one 5(S)-[ 1 (S)-Methyl]propyl-2,3,5,6-tetrahydro-4H- 1,4-oxazin- 3-one (12.2 g, 0.0776 mol) and DMAP (18.9 g, 0.155 mol) were dissolved in methylene chloride (120 ml) under argon at R.T. Boc anhydride (33.9 g, 0.155 mol) was added to the stirred solution in one portion, with concomitant gas evolution and the mixture was stirred at R.T. for 16 hr. The solvent was evaporated in vacuo and the residue was taken up in ethyl acetate and washed sequentially with 10% citric acid, 5% $NaHCO_3$ and finally brine. The organic extract was dried ($Na_2SO_4$) and evaporated in vacuo. Chromatography of the residue over silica gel eluting with 20% EtOAc in hexanes afforded the title compound as a white solid.

Rf=0.75 EtOAc:hexanes (20:80); mp 59°–60° C. Anal. Calcd for $C_{13}H_{23}O_4N$: C, 60.68; H,9.01; N, 5.44. Found: C, 60.75; H, 9.01; N, 5.58.

$^1H$ NMR (CDCl$_3$) δ4.25 (1H, d, J=15 Hz), 4.15 (1H, d, J=15 Hz), 4.15–4.00 (2H, m), 3.73 (1H, dd, J = 10 and 2 Hz), 1.88 (1H, qt, J=6 Hz), 1.55 (9H, s), 1.50–1.36 (1H, m), 1.35–1.19 (1H, m) 1.00 (3H, d, J=6 Hz) 0.95 (3H, d, J=6.5 Hz).

Step D. Preparation of N-(tert-Butoxycarbonyl)-2(R)-(1-hydroxy- 1-methyl)ethyl-5(S)-[1(S)-methyl]propyl-2,3,5,6-tetrahydro-4H- 1,4oxazin-3-one A solution of a N-(tert-butoxycarbonyl)-5(S)-[ 1 (S)-methyl]propyl- 2,3,5,6-tetrahydro-4H-1,4-oxazin-3-one (0.5 g, 1.94 mmol) in DME (6 ml) was cooled to −60° C. and transferred under argon via a cannula to a flask containing a solution of NaHMDS (1.0M in THF, 2.14 ml, 2.14 mmol) at −78° C. The resulting mixture was stirred for 5 mins, acetone (0.16 ml, 2.14 mmol) was added and stirred at −78° C. for 4 h. The reaction mixture was treated with saturated aqueous ammonium chloride (2.14 ml), brine (4 ml) and water (1 ml). Then, it was extracted with ether (210 ml). The combined extracts were dried, filtered and evaporated to yield a residue. Purification of the residue by flash chromatography afforded the title compound as an oil.

NMR (CDCl$_3$) δ0.93 (3H, t, J=7Hz,), 1.00 (3H, d, J=7Hz), 1.27 (3H, s), 1.28 (3H, s), 1.54 (9H, s), 1.82 (H, m), 3.73 (H, m), 3.8–4.0 (2H, m), 4.0–4.25 (2H, m), 4.58 (H, m).

Step E. Preparation of N-(tert-Butoxycarbonyl-2-isopropylidenyl- 5(S)-[1(S)-methyl]-propyl-2,3,5,6-tetrahydro-4H- 1,4-oxazin-3-one A solution of N-tert-butoxycarbonyl)-2(R)-( 1 -hydroxy-1 -methyl)ethyl- 5(S)-[1(S)-methyl]propyl-2,3,5,6-tetrahydro-4H- 1,4-oxazin-3-one (0.597 g, 1.26 mmol) in pyridine (20 ml) was cooled to 0° C. and treated with phosphorus oxychloride (1.23 ml) and the resulting mixture was allowed to warm to room temperature and stirred overnight. The reaction mixture was treated with saturated sodium bicarbonate solution (50 ml) and extracted with methylene chloride three times. The combined extracts were washed with brine (15 ml), dried, filtered and evaporated to give a residue which was purified by flash chromatography to yield the title compound.

NMR (CDCl$_3$) δ 0.91 (3H, t, J=7Hz), 0.97 (3H, d, J=7Hz), 1.20 (H, m), 1.54 (9H, s), 1.80 (3H, s), 2.14 (3H, s), 3.93 (H, d of d, J=12, 3Hz), 4.07 (H, t of d, J=8, 2Hz), 4.23 (H, d of d, J=1 2, 4Hz).

Step F. Preparation of N-(tert-Butoxycarbonyl-2-(S)-isopropyl-5(S)-[1 (S)-methyl]propyl- 2,3,5,6-tetrahydro-4H-1,4-oxazin-3-one A mixture of N-(tert-butoxycarbonyl)-2-isopropylidenyl-5(S)-[1 (S)-methyl]propyl-2,3,5,6-4H-1,4-oxazin-3-one (0.19 g, 0.63 mmol) and $PtO_2$ (20 mg) in ethyl acetate (20 ml) was hydrogenated on a Parr shaker for 5 h at 54 psi. The reaction mixture was filtered through a pad of Celite and the flitrate was evaporated to give the title compound as an oil.

NMR (CDC13) 15 0.92 (3H, t, J=Hz), 0.93 (3H, d, J=7Hz), 0.99 (3H, d, J=7Hz), 1.0.4 (3H, d, J=7Hz, 1.53 (9H, s), 1.84 (H, m), 2.47 (H, m), 3.67 (H, d of d, J=1 4, 4Hz), 3.90 (H, d, J=3Hz), 3.92 (H, m), 4.11 (H, d, J=14Hz).

Step G. Preparation of N-(tert-butoxycarbonyl)-2(S)-[2(S)-amino- 3(S)-methyl]pentyloxy-3-methylbutyric acid A solution of N-(tert-butoxycarbonyl)-2(S)-isopropyl-5(S)-[ 1(S)-methyl]-propyl-2,3,5,6-tetrahydro-4H- 1,4-oxazin-3-one (2.4 g, 7.2 mmol) in glacial acetic acid was treated with concentrated hydrochloric acid and heated to reflux overnight. The solvent was evaporated in vacuo and the residue was azeotropically dried with toluene (50 mL) and acetonitrile (50 mL). After drying 1 h under vacuum at room temperature, the residue was dissolved in 100 mL of 50% aqueous acetone, 3.15 g of $Boc_2O$ was added and the pH was adjusted to approximately 10 with 1 N NaOH. After the reaction was complete, the solution was acidified with citric acid and the product was extracted into ethyl acetate. The extracted product was purified by chromatography over silica gel eluting with 5–10% MeOH in $CH_2Cl_2$ to give the title compound.

Step H. Preparation of N-(tert-Butoxycarbonyl)-2(S)-[2(S)-amino- 3(S)-methyl]-pentyloxy-3-methylbutyryl-leucine methyl ester To a stirred solution of N-(tert-butoxycarbonyl)-2(S)-[2(S)-amino-3(S)-methyl]-pentyloxy-3-methylbutyric acid (0.200 g, 0.63 mmol) and EDC (0.191 g, 1.0 mmol) in DMF (3 ml) at room temperature was added HOOBT (163 mg, 1.0 mmol) and leucine methyl ester hydrochloride (0.182 g, 1.0 mmol). Triethylamine (0.28 mL, 2 mmol) was added. After stirring at room temperature for 16 hr, the reaction was diluted with EtOAc and washed with water and brine and dried ($NaSO_4$). Evaporation in vacuo and chromatography over silica gel eluting with EtOAc/methylene chloride (0–20%) afforded the title compound.

Step I. Preparation of N-[2(S)-(2(S)-(2(R)-amino-3-mercaptopropylamino)- 3(S)-methylpentyloxy)-3-methylbutanoyl]-leucine methyl ester;

The t-butoxycarbonyl protecting group of the product of Step H was removed by treating a solution of the compound with hydrogen chloride in ethyl acetate. Using the methods of Example 1, the hydrochloride thus obtained was converted to the title compound.

Anal. Calcd for $C_{21}H_{43}N_3O_4S \cdot 2.1$ TFA: C, 44.94; H, 6.75; N, 6.24. Found: C, 45.00; H, 6.64; N, 6.34.

Example 6

N-[2(S)-(2(S)-(2(R )-amino-3-mercaptopropylamino )-3(S)-methylpentyloxy)-3-methylbutanoyl]-leucine;

Using the appropriate intermediate from Example 5 and the method of Example 2, the title compound was prepared.

Anal. Calcd for $C_{20}H_{41}N_3O_4S \cdot 2.0$ TFA: C, 44.30; H, 6.64; N, 6.43. Found: C, 44.28; H, 6.60; N, 6.45.

Example 7

In vitro inhibition of geranylgeranyl protein transferase type I

*Purification of isoprenyl-protein transferases*. All purification steps were performed at 4 ° C. Cerebral lobes from bovine brains were homogenized in lysis buffer containing 50 mM Tris-Cl, pH 8.0, 1 mM EGTA, 1 mM $MgCl_2$, 5 mM dithiothreitol, 10 μg/mL aprotinin, 0.5 mM phenylmethyl sulfonyl fluoride (PMSF), 2 μg/mL antipain and 2 μg/mL leupeptin (M.D. Schaber et al. *J. Biol. Chem.*, 265:14701 (1990)). Cellular debris and membranes were removed by centrifugation (10 000 g for 20 rain followed by 100 000 g for 30 minutes). The supernatant was loaded directly onto a column (30 cm × 20 $cm^2$) of DEAE-Sephacel that had been equilibrated with lysis buffer. The column was washed with the same buffer and proteins were eluted with a linear gradient of NaCl (0–500 mM, 1 L+L) in the same buffer. Fractions (20 mL) were collected and those containing different transferase activities were pooled separately. This procedure resolved FTase and GGPTase-II from GGPTase-I. Each pool was then applied to an ω-Aminooctyl agarose colurctn (30 cm×4.9 $cm^2$) and eluted with a linear gradient of NaCl (0–500 mM, 500 mL+500 mL) in lysis buffer. Fractions containing both FTase and GGPTase-II were pooled. The GGPTase-I (termed "bGGPTase-I") so obtained was utilized in the assay described below.

*Cloning of human GGPTase-I βGGI subunit cDNAs*. Approximately 1 nmol of GGPTase-I-I purified from bovine brain as described in Moomaw, J.F. and ,Casey, P.J. (1992) *J Biol Chem* 267:17438–17443, was subjected to electrophoresis on a 11% SDS-polyacrylamide gel and transferred to nitrocellulose paper. The nitrocellulose paper was then stained with Poneeau S to localize the subunit polypeptides. The 48 kDa and 43 kDa bands were excised from the nitroeellulose and sent to Harvard Microchem (Cambridge, Mass.) for processing. High-confidence sequences of five βGGI subunit peptides were obtained. The sequences of these peptides are listed below:

| $β_{GGI}$ peptide | Amino Acid Sequence | Location of peptide (aa) aa) human $β_{GGI}$ open reading frame |
| --- | --- | --- |
| 1 | TIAFFALSGLDMLD (SEQ.ID.NO.:1) | 48–61 |
| 2 | GSSYLGIPFNPSK (SEQ.ID.NO.:2) | 96–108 |
| 3 | IFQYTNFEK (SEQ.ID.NO.:3) | 284–292 |
| 4 | NYILSTQDR (SEQ.ID.NO.:4) | 295–303 |
| 5 | DLHQSWK (SEQ.ID.NO.:5) | 355–361 |

Two degenerate oligonucleotide primers [GCTC-GGATCC-C-(A/G)AA-(A/G)TT-NGT-(A/G)TA-(T/C)TG-(A/G)A (SEQ.ID.NO.:6) and GTCGG-GAATTC-ACN-AT(A/C/T)-GCN-TT(C/T)-TT(C/T)-GC (SEQ.ID.NO.:7)] were synthesized based on portions of two βGGI subunit peptide sequences [IFQYTNFEK (SEQ.ID.NO.:3) (antisense oligo) and TIAFFLSGLDMLD (SEQ.ID.NO.:I) respectively]. The polymerase chain reaction (PCR) (Saiki, R. K., Gelfand, D. H., Stoffel, S., Scharf, S. J., Higuchi, R., Horn, G. T., Mullis, K. B. and Erlich, H. A. (1988) *Science* 239:487– 463) was performed using DNA obtained from a bovine brain eDNA library as template (Vogel, U.S., Dixon, R. A. F., Schaber, M.D., Diehl, R. E., Marshall, M. S., Scoinick, E. M., Sigal, I. S. and Gibbs, J. B. (1988) *Nature* 335:90–93). A 730 bp PCR product was isolated that hybridized to a degenerate oligonucleotide [GTAC-TCTAGA-GGN-AT(A/C/T)- CCN-TT(T/C)-AA(T/C)-CC (SEQ.ID.NO.:8)] encoding part of the peptide GSSYL-GIPFNPSK. The PCR product is shown in FIG. 1. (SEQ.ID.NO.:9) The PCR fragment was cleaved with EcoRI and BamHI, sites for which were in the PCR oligos, and cloned into pUC18 creating pRD548.

To isolate human cI)NAs encoding the βGGI subunit a 300 bp EcoRI-HindIII fragment containing the N-terminal portion of the coding sequence in pRD548 was [$^{32}$P]-labelled and used to screen approximately $10^6$ plaques each from both a human placenta eDNA library in λgt11 (Clonetech) and a human kidney eDNA library in λmax1 (Clonetech) as described (Kohl, N. E., R. E. Diehl, M. S. Schaber, E. Rands, D. D. Sodennan, B. He, S. L. Moores, D. L. Pompliano, S. Ferro-Novick, S. Powers, K. A. Thomas and J. B. Gibbs. 1991. *J. Biol. Chem.* 266: 18884–18888.). Six eDNA clones were isolated from the human placenta eDNA library and seven were isolated from the human kidney eDNA library. Phage from the λgt11 library were isolated and the cDNA inserts subcloned into pUC18 as EcoRI fragments. cDNA inserts from clones from the λmax1 library were exised as phagemids. A plasmid containing the 1.55 kb cDNA from clone 3 from the human placenta cDNA library was designated pRD550. The insert in pRD550 contains all but the N-terminal 36 codons for βGGI. The phagemid containing the 0.7 kb cDNA from clone 27 from the human kidney cDNA library was designated pRD558. The insert in pRD558 encodes the N-terminal 123 amino acids of βGGI. To construct a plasmid with the complete human βGGI coding sequence the following was done. PCR was performed on pRD558 placing a BamHI and ScaI site upstream of the βGGI start codon. This DNA was cleaved with BamHI and XhoI, which cleaves within the βGGI coding sequence, creating fragment 1 of 0.13 kb. Fragment 2 was a 1.52 kb XhoI-EcoRI fragment from pRD550 that contained the coding sequence downstream of the XhoI site. Fragments 1 and 2 were cloned into BamHI-EcoRI digested pUC18 creating pRD566 which contains the complete coding sequence for human βGGI and 3'-untranslated sequences. The sequence is shown in FIG. 2 (SEQ.ID.NO.: 10).

Expression of human GGPTase-I (hGGPTase-1) in *E. coli*: To express human GGPTase-I in *E. coli* the cloned human βGGI subunit cDNA and the previously cloned human FTase-α subunit cDNA (Omer, C. A., A.M. Kral, R. E. Diehl, G. C. Prendergast, S. Powers, C. M. Allen, J. B. Gibbs and N. E. Kohl. 1993. *Biochem.* 32:5167–5176) were coexpressed in a translationally coupled operon. In *E. coli*, the plasmid pT5T-hFPTase-α expresses the human α subunit protein with a C-terminal Glu-Glu-Phe epitope tag from a bacteriophage T7 promoter. The coding sequence for the human βGGI protein was cloned downstream of the α subunit coding sequence in pT5T-hFPTase-α as follows. Fragment 1, a 0.5 kb SpeI-XhoI fragment, containing the sequence CT between the C-terminus of α and the N-terminus of the βGGI subunit coding sequences was made by recombinant PCR using pT5T-hFPTase-α and pRD566 as templates (Higuchi, R.(1990) in PCR Protocols: A Guide to Methods and Applications (Innis, M.A., Gelfand, D. H., Sninsky, J. J, & White, T. J., eds.), pp. 177–183, Academic Press, San Diego). Fragment 2, a 1.52 kb XhoI-EcoRI fragment from pRD566 contained the part of the βGGI coding sequence not in fragment 1. Fragment 3 was a 6.2 kb SpeI (partial digestion)-EcoRI fragment from pT5T-hF-PTase-α that contained the portion of the α coding sequence not in fragment 1 and the vector and promoter sequences from pT5T-hFPTase-α. Fragments 1, 2 and 3 were ligated together to create pRD577 which has the following structure:

N. E. (1993) *Biochemistry* 32:5167–5176). Recombinant, human GGPTase-I (termed "hGGPTase-I") was purified from the cells essentially as described for human FTase using a YL½ antibody column, which binds the Glu-Glu-Phe epitope tag on the α subunit, and an optional MonoQ HR 5/5 column (Omer, C.A. et al. (1993)). The hGGPTase-I eluted from the MonoQ column at approximately 0.25M NaCl.

*Molecular biological manipulations.* To construct the C-terminus CAAX box routants, pUC-[L68]RAS1(term.) was digested with the restriction enzymes HincII and NarI to create a vector into which oligonucleotides containing new C-terminal sequences could be ligated. Except where indicated, the amino acids preceding the CAAX sequence are SLK. To simplify the nomenclature, [L68]RAS1 (term.)SLKCVLS (J.B. Gibbs et al., *Proc. Natl. Acad Sci. U.S.A.*, 86:6630 (1989)) will be referred to as Ras-CVLS, and this convention is used for all other mutants. The substrate for Frase was Ras-CVLS. The substrate for GGPTase-I was Ras-CAIL.

*Transferase Assays.* Isoprenyl-protein transferase activity assays were carried out at 30 °C. unless noted otherwise. A typical reaction contained (in a final volume of 50 μL): [$^3$H]farnesyl diphosphate or [$^3$H]geranylgeranyl diphosphate, Ras protein, 50 mM HEPES, pH 7.5, 5 mM $MgCl_2$, 5 mM dithiothreitol and isoprenyl-protein transferase. The FPTase employed in the assay was prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. After thermally pre-equilibrating the assay mixture in the absence of enzyme, reactions were initiated by the addition of isoprenyl-protein transferase and stopped at timed intervals (typically 15 min) by the addition of 1M HCl in ethanol (1 mL). The quenched reactions were allowed to stand for 15 m (to complete the precipitation process). After adding 2 mL of 100% ethanol, the reactions were vacuum-filtered through Whatman GF/C filters. Filters were washed four times with 2 mL aliquots of 100% ethanol, mixed with scintillation fluid (10 mL) and then counted in a Beckman LS3801 scintillation counter.

For inhibition studies, assays were run as described above, except inhibitors were prepared as concentrated solutions in 100% dimethyl sulfoxide and then diluted 20-fold into the enzyme assay mixture. $IC_{50}$ values were determined with both transferase substrates near $K_M$ concentrations. Nonsaturating substrate conditions for inhibitor $IC_{50}$ determinations were as follows: FTase, 650 nM Ras-CVLS, 100 nM farnesyl diphosphate; GGPTase-I, 500 nM Ras-CAIL, 100 nM geranylgeranyl diphosphate.

```
                    RBS
pT5T -  α coding —GAG—GAG—TTT—TAA—CTT—ATG—GTA—   βGGI coding
                —Glu—Glu—Phe—stop        Met—Val—
```

[internal base sequence: (SEQ.ID.NO.:I 1)]. The coding sequence for the human βGGI subunit was translationally coupled to the a subunit coding sequence with the ribosomal binding site (RBS), for expression of βGGI, within the Glu-Glu-Phe epitope tag.

To express human GGPTase-I, pRD577 was transformed into *E. coli* BL21(DE3), creating strain RD578, grown and induced with 0.5 mM isopropyl-β-D-thiogalactoside as described (Omer, C. A., Kral, A. M., Diehl, R. E., Prende, rgast, G. C., Powers, S., Allen, C. M., Gibbs, J. B. and Kohl,

TABLE 1

Inhibition of protein geranylgeranylation and protein farnesylation by compounds of this invention*

| Compound | $IC_{50}(nM)$* bGGPTase-I | hGGPTase-I | FPTase |
|---|---|---|---|
| N-(2(R)-amino-3-mercaptopropyl)-valyl-isoleucyl-leucine; | 1.9 | 23 | 800 |
| N-[5(S)-(2(R)-amino-3-mercaptopropyl-amino)-6(S)-methyl-2(R)-isopropyl-3,4(E)-heptenoyl]-leucine; | 21 | | 70 |
| N-[2(S)-(2(S)-(2(R)-amino-3-mercapto-propylamino)-3(S)-methylpentyloxy)-3-methylbutanoyl]-leucine; | 37 | | 450 |

*$IC_{50}$ is the concentration of the test compound which gives 50% inhibition of FTase or GGPTase-I under the described assay conditions.

---

What is claimed is:

1. A compound which inhibits geranylgeranyl protein transferase type I, and is a selectively more potent inhibitor of geranylgeranyl protein transferase than of farnesyl protein transferase, having the formula I:

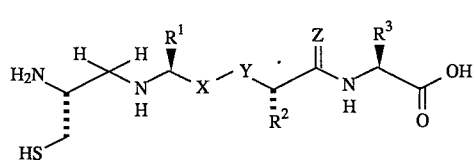

wherein:

R$^1$ and R$^2$ are independently selected from:
  a) C$_2$–C$_8$ alkyl;
  b) C$_2$–C$_8$ alkenyl;
  c) C$_2$–C$_8$ alkynyl;
  d) substituted C$_1$–C$_8$ alkyl;
  e) aryl;
  f) substituted aryl;
  g) heteroaryl;
  h) substituted heteroaryl; and
  i) the side chain of a naturally occurring amino acid;

R$^3$ is selected from alkyl, alkenyl and alkynyl of 1 to 6 carbon atoms, either branched or straight chain, which is unsubstituted or substituted with a phenyl group;

X—Y is

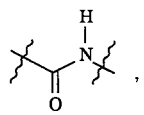

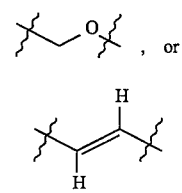

and Z is H$_2$ or O;
or the pharmaceutically acceptable salts thereof.

2. A prodrug of a compound of claim 1 having the formula II:

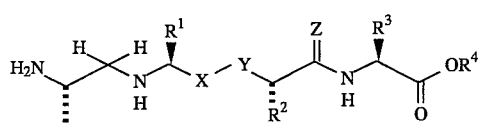

wherein:

R$^1$ and R$^2$ are independently selected from:
  a) C$_2$–C$_8$ alkyl;
  b) C$_2$–C$_8$ alkenyl;
  c) C$_2$–C$_8$ alkynyl;
  d) substituted C$_1$–C$_8$ alkyl;
  e) aryl;

f) substituted aryl;
g) heteroaryl;
h) substituted heteroaryl; and
i) the side chain of a naturally occurring amino acid;

$R^3$ is selected from alkyl, alkenyl and alkynyl of 1 to 6 atoms either branched or straight chain which is unsubstituted or substituted with a phenyl group;

X—Y is

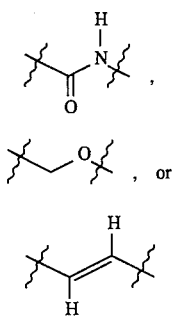

a)

b)

c)

$R^4$ is selected from:
a) $C_1$–$C_8$ alkyl;
b) $C_3$–$C_8$ alkenyl;
c) $C_3$–$C_8$ alkynyl;
d) substituted $C_1$–$C_8$ alkyl;
e) aryl;
f) substituted aryl;
g) heteroaryl; and
h) substituted heteroaryl;

and Z is $H_2$ or O;

or a pharmaceutically acceptable salt thereof.

3. A compound which inhibits geranylgeranyl-protein transferase type I which is:

N-(2(R)-amino-3-mercaptopropyl)-valyl-isoleucyl-leucine;

N-(2(R)-amino-3-mercaptopropyl)-valyl-isoleucyl-leucine methyl ester;

N-[5(S)-(2(R)-amino-3-mercaptopropylamino)-6(S)-methyl-2-(R)-isopropyl-3,4(E)-heptenoyl]-leucine;

N-[5 (S)-(2(R)-amino-3 -mercaptopropylamino)-6(S)-methyl-2(R)-isopropyl-3,4(E)-heptenoyl]-leucine methyl ester;

N-[2(S)-(2(S)-(2(R)-animo-3-mercaptopropylamino)-3(S)-methylpentyloxy)-3-methylbutanoyl]-leucine;

N-[2(S)-(2(S)-(2(R)-amino-3-mercaptopropylamino)-3(S)-methylpentyloxy)-3-methylbutanoyl]-leucine methyl ester;

or the pharmaceutically acceptable salts thereof.

4. The compound according to claim 1 which is:

N-(2(R)-amino-3-mercaptopropyl)-valyl-isoleucyl-leucine;

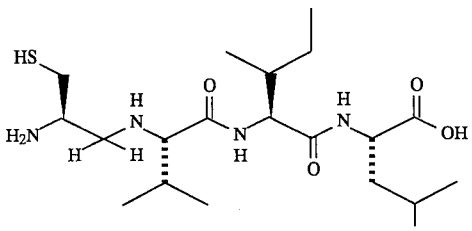

or a pharmaceutically acceptable salt thereof.

5. A prodrug of a compound which inhibits geranylgeranyl-protein transferase type I according to claim 2 which is:

N-(2(R)-amino-3-mercaptopropyl)-valyl-isoleucyl-leucine methyl ester;

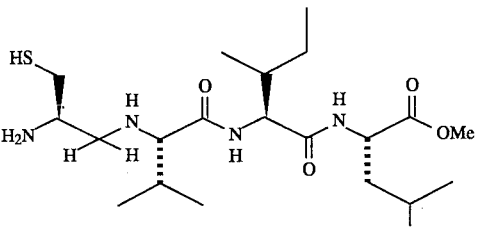

or a pharmaceutically acceptable salt thereof.

6. A pharmaceutical composition comprising a therapeutically effective amount of a compound of claim 1 and a pharmaceutically acceptable carrier.

7. A pharmaceutical composition comprising a therapeutically effective amount of a compound of claim 2 and a pharmaceutically acceptable carrier.

8. A method of inhibiting the geranylgeranylation of proteins by geranylgentnyl protein transferase type I in a patient in need of such inhibition which comprises administering to the patient a pharmaceutically effective amount of the composition of claim 6.

9. A method of treating an inflammatory disease in a patient in need of such treatment which comprises administering to the patient a pharmaceutically effective amount of the composition of claim 6.

10. A method of treating an inflammatory disease in a patient in need of such treatment which comprises administering to the patient a pharmaceutically effective amount of the composition of claim 7.

* * * * *

UNITED STATES PATENT AND TRADEMARK OFFICE
CERTIFICATE OF CORRECTION

PATENT NO. : 5,470,832

DATED : November 28, 1995

INVENTOR(S) : Jackson B. Gibbs and Samuel L. Graham

It is certified that error appears in the above-identified patent and that said Letters Patent is hereby corrected as shown below:

At Column 33, in Claim 2, line 33 (last sentence), should read as follows:

or a pharmaceutically acceptable salt thereof.

At Column 33, in Claim 3, line 43 should read as follows:

N-[5(S)-(2(R)-amino-3-mercaptopropylamino)-6(S)-methyl-2(R)-isopropyl-3,4(E)-heptenoyl]-leucine methyl ester;

At Column 34, in Claim 8 should read as follows:

A method of inhibiting the geranylgeranylation of proteins by geranylgeranyl protein transferase type I in a patient in need of such inhibition which comprises administering to the patient a pharmaceutically effective amount of the composition of claim 6.

Signed and Sealed this

Thirtieth Day of July, 1996

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Thr  Ile  Ala  Phe  Phe  Ala  Leu  Ser  Gly  Leu  Asp  Met  Leu  Asp
1                 5                          10
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Gly  Ser  Ser  Tyr  Leu  Gly  Ile  Pro  Phe  Asn  Pro  Ser  Lys
1                 5                          10
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Ile  Phe  Gln  Tyr  Thr  Asn  Phe  Glu  Lys
1                 5
```

( 2 ) INFORMATION FOR SEQ ID NO:4:

( i ) SEQUENCE CHARACTERISTICS:

( A ) LENGTH: 9 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

Asn Tyr Ile Leu Ser Thr Gln Asp Arg
1               5

( 2 ) INFORMATION FOR SEQ ID NO:5:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

Asp Leu His Gln Ser Trp Lys
1               5

( 2 ) INFORMATION FOR SEQ ID NO:6:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

GCTCGGATCC CRAARTTNGT RTAYTGRA                           2 8

( 2 ) INFORMATION FOR SEQ ID NO:7:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

GTCGGAATTC ACNATHGCNT TYTTYGC                            2 7

( 2 ) INFORMATION FOR SEQ ID NO:8:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

GTACTCTAGA GGNATHCCNT TYAAYCC                            2 7

( 2 ) INFORMATION FOR SEQ ID NO:9:

( i ) SEQUENCE CHARACTERISTICS:
( A ) LENGTH: 729 base pairs
( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:9:

| | | | | | | |
|---|---|---|---|---|---|---|
| ACGATAGCGT | TTTTTGCACT | CTCCGGGCTG | GATATGTTGG | ATTCCTTAGA | TGTGGTGAAC | 60 |
| AAAGATGATA | TAATAGAGTG | GATTTATTGG | GTGCAGGTCC | TTCCCACAGA | AGACAGATCA | 120 |
| AATCTAAATC | GCTGTGGTTT | CCGAGGCTCT | TCATACCTGG | GTATTCCGTT | CAATCCATCA | 180 |
| AAGGCTCCTG | GAACAGCTCA | TCCTTATGAT | AGTGGCCACA | TTGCAATGAC | CTACACTGGC | 240 |
| CTCTCATGCT | TAGTTATTCT | TGGAGACGAC | TTAAGCCGAG | TAAATAAAGA | AGCTTGCTTA | 300 |
| GCGGGCTTGA | GAGCCCTTCA | GCTGGAAGAT | GGGAGTTTTT | GTGCAGTACC | TGAAGGCAGT | 360 |
| GAAAATGACA | TGCGATTTGT | GTACTGTGCT | TCCTGTATTT | GCTATATGCT | CAACAACTGG | 420 |
| TCAGGCATGG | ATATGAAAAA | GCCATCACCT | ATATTAGAAG | GAGTATGTCC | TATGACAATG | 480 |
| GACTGGCACA | GGGAGCTGGA | CTTGAATCTC | ATGGAGGATC | AACTTTTGT | GGCATTGCCT | 540 |
| CACTATGTCT | GATGGGTAAA | CTAGAAGAAG | TTTTTCAGA | AAAAGAATTG | AACAGGATAA | 600 |
| AGAGGTGGTG | TATAATGAGG | CAACAAAATG | GTTATCATGG | AAGACCTAAT | AAGCCTGTAG | 660 |
| ACACCTGTTA | TTCTTTTTGG | GTGGGAGCAA | CTCTGAAGCT | TCTAAAAATT | TTCCAATACA | 720 |
| CCAACTTCG | | | | | | 729 |

(2) INFORMATION FOR SEQ ID NO:10:

(i) SEQUENCE CHARACTERISTICS:
(A) LENGTH: 1670 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

| | | | | | | |
|---|---|---|---|---|---|---|
| GGATCCAGTA | CTTATGGTAG | CCACTGAGGA | TGAGAGGCTA | GCAGGGAGCG | GTGAGGGAGA | 60 |
| GCGGCTGGAT | TTCTTACGGG | ATCGGCACGT | GCGATTTTTC | CAGCGCTGCC | TCCAGGTTTT | 120 |
| GCCGGAGCGC | TATTCTTCAC | TCGAGACAAG | CAGGTTGACA | ATTGCATTTT | TTGCACTCTC | 180 |
| CGGGCTGGAT | ATGTTGGATT | CCTTAGATGT | GGTGAACAAA | GATGATATAA | TAGAGTGGAT | 240 |
| TTATTCCCTG | CAGGTCCTTC | CCACAGAAGA | CAGATCAAAT | CTAAATCGCT | GTGGTTTCCG | 300 |
| AGGCTCTTCA | TACCTGGGTA | TTCCGTTCAA | TCCATCAAAG | GCTCCTGGAA | CAGCTCATCC | 360 |
| TTATGATAGT | GGCCACATTG | CAATGACCTA | CACTGGCCTC | TCATGCTTAG | TTATTCTTGG | 420 |
| AGACGACTTA | AGCCGAGTAA | ATAAAGAAGC | TTGCTTAGCG | GGCTTGAGAG | CCCTTCAGCT | 480 |
| GGAAGATGGG | AGTTTTGTG | CAGTACCTGA | AGGCAGTGAA | AATGACATGC | GATTTGTGTA | 540 |
| CTGTGCTTCC | TGTATTTGCT | ATATGCTCAA | CAACTGGTCA | GGCATGGATA | TGAAAAAGC | 600 |
| CATCACCTAT | ATTAGAAGGA | GTATGTCCTA | TGACAATGGA | CTGGCACAGG | GAGCTGGACT | 660 |
| TGAATCTCAT | GGAGGATCAA | CTTTTTGTGG | CATTGCCTCA | CTATGTCTGA | TGGGTAAACT | 720 |
| AGAAGAAGTT | TTTCAGAAA | AGAATTGAA | CAGGATAAAG | AGGTGGTGTA | TAATGAGGCA | 780 |
| ACAAAATGGT | TATCATGGAA | GACCTAATAA | GCCTGTAGAC | ACCTGTTATT | CTTTTTGGGT | 840 |
| GGGAGCAACT | CTGAAGCTTC | TAAAAATTTT | CCAATACACT | AACTTTGAGA | AAAATAGAAA | 900 |
| TTACATCTTA | TCAACTCAAG | ATCGCCTTGT | AGGGGGATTT | GCCAAGTGGC | CAGACAGTCA | 960 |
| TCCAGATGCT | TTGCATGCAT | ACTTTGGGAT | CTGTGGCCTG | TCACTAATGG | AGGAAAGTGG | 1020 |

| | | | | | | |
|---|---|---|---|---|---|---|
| AATTTGTAAA | GTTCATCCTG | CTCTGAATGT | AAGCACACGG | ACTTCTGAAC | GCCTTCTAGA | 1080 |
| TCTCCATCAA | AGCTGGAAAA | CCAAGGACTC | TAAACAATGC | TCAGAGAATG | TACATATCTC | 1140 |
| CACATGACTG | ATTTTAGATT | GGGAGGGTGG | GGGGGATTTG | TAGCATAACT | GTAGCTCAAG | 1200 |
| TTTAAAAGCC | ATGTATAACC | AAGTGTGCTC | TTTTTTTAAA | AGGTAGAGTC | TTACAATCAA | 1260 |
| ATCTCCTGCT | GATTTCACTT | TGGGATATGG | TCTTGAGCCA | GTAATCTTTA | TACTGGGTTT | 1320 |
| CAAGAAAATC | TTTGTTGAAG | TTTGAACCAC | AACTTTGTCG | TGGTTCTTAA | ATGTTTATAC | 1380 |
| TGTATTTCTA | AGAAGTTGTT | TGAGGCAAAT | TAACTGTATG | TGTGTAGGTT | ATCTTTTTAA | 1440 |
| AAACTCTTCA | GTGCAAATTG | TATCTTATTA | TAAAATGGAC | ACAAATTTTC | AAGTTTACAC | 1500 |
| TTCATATAGC | ATTGATAATC | TTCAGGTGAA | CACTTAGTGA | TCATTAAAA | AGCTCACTGC | 1560 |
| TGATCGTAGA | AAATTTGCTT | TAATTAATTA | AGTATCTGGG | ATTATTCTTT | GAAACAGAT | 1620 |
| GACCATAATT | TTTTTAAAG | AAGAGTGACT | TATTTGTCT | TATTCTTAAG | | 1670 |

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GAGGAGTTTT AACTTATGGT A　　　　　　　　　　　　　　　　21